United States Patent
Finan et al.

(10) Patent No.: US 11,497,851 B2
(45) Date of Patent: Nov. 15, 2022

(54) MAINTAINING MAXIMUM DOSING LIMITS FOR CLOSED LOOP INSULIN MANAGEMENT SYSTEMS

(71) Applicant: LifeScan IP Holdings, LLC, Malvern, PA (US)

(72) Inventors: Daniel Finan, Philadelphia, PA (US); Pavel Vereshchetin, Moscow (RU)

(73) Assignee: Lifescan IP Holdings, LLC, Malvern, PA (US)

( * ) Notice: Subject to any disclaimer, the term of this patent is extended or adjusted under 35 U.S.C. 154(b) by 3 days.

(21) Appl. No.: 15/475,188

(22) Filed: Mar. 31, 2017

(65) Prior Publication Data

US 2018/0280619 A1    Oct. 4, 2018

(51) Int. Cl.
| | |
|---|---|
| *A61M 5/172* | (2006.01) |
| *A61M 5/142* | (2006.01) |
| *G16H 40/63* | (2018.01) |
| *G16H 20/17* | (2018.01) |
| *G16H 50/30* | (2018.01) |
| *G16H 50/20* | (2018.01) |

(52) U.S. Cl.
CPC ...... *A61M 5/1723* (2013.01); *A61M 5/14244* (2013.01); *G16H 20/17* (2018.01); *G16H 40/63* (2018.01); *G16H 50/20* (2018.01); *G16H 50/30* (2018.01); *A61M 2005/14208* (2013.01); *A61M 2205/3561* (2013.01); *A61M 2230/201* (2013.01)

(58) Field of Classification Search
CPC ............ A61B 5/14532; A61B 5/14865; A61B 5/1495; A61B 5/0002; A61B 5/0031; A61B 5/4839; G06F 19/00; G06F 19/3468; G06F 19/3418; G06F 19/3456; C12Q 1/006; A61M 5/1723; A61M 2230/201; A61M 5/14244
See application file for complete search history.

(56) References Cited

U.S. PATENT DOCUMENTS

| | | | |
|---|---|---|---|
| 7,060,059 | B2 | 6/2006 | Keith et al. |
| 7,276,029 | B2 | 10/2007 | Goode, Jr. et al. |

(Continued)

FOREIGN PATENT DOCUMENTS

| | | |
|---|---|---|
| CA | 2 683 504 C | 2/2013 |
| CN | 104756116 A | 7/2015 |

(Continued)

OTHER PUBLICATIONS

King, Allen B., and Dana U. Armstrong. "A Prospective Evaluation of Insulin Dosing Recommendations in Patients with Type 1 Diabetes at Near Normal Glucose Control: Basal Dosing." Journal of diabetes science and technology (Online) 1.1 (2007): 36-41. Print.*

(Continued)

*Primary Examiner* — Scott J Medway
(74) *Attorney, Agent, or Firm* — Barclay Damon LLP (57) ABSTRACT

A system and a method for management of diabetes are provided. The system includes an infusion pump, glucose sensor, and controller that is programmed to control insulin delivery based upon at least one stored variable. The controller calculates a maximum insulin delivery rate based on the default basal insulin delivery rate, temporary basal insulin delivery rate, extended bolus rate, or a combination thereof.

10 Claims, 5 Drawing Sheets

(56) References Cited

U.S. PATENT DOCUMENTS

| | | | |
|---|---|---|---|
| 7,806,854 | B2 | 10/2010 | Damiano et al. |
| 8,454,576 | B2 | 6/2013 | Mastrototaro et al. |
| 8,562,587 | B2 | 10/2013 | Kovatchev et al. |
| 8,579,879 | B2 | 11/2013 | Palerm et al. |
| 8,762,070 | B2 | 6/2014 | Doyle, III et al. |
| 2003/0050621 | A1* | 3/2003 | Lebel .................... A61M 5/172 128/920 |
| 2010/0156633 | A1* | 6/2010 | Buck, Jr. ........... A61M 5/14244 707/661 |
| 2011/0098638 | A1 | 4/2011 | Chawla et al. |
| 2011/0257627 | A1 | 10/2011 | Hovorka |
| 2011/0313390 | A1 | 12/2011 | Roy et al. |
| 2011/0313680 | A1 | 12/2011 | Doyle, III et al. |
| 2012/0078067 | A1* | 3/2012 | Kovatchev ............. G16H 20/17 600/301 |
| 2012/0136336 | A1 | 5/2012 | Mastrototaro et al. |
| 2012/0191061 | A1* | 7/2012 | Yodfat .................. A61M 5/172 604/503 |
| 2012/0283694 | A1 | 11/2012 | Yodfat et al. |
| 2013/0131630 | A1 | 5/2013 | Blomquist |
| 2013/0231642 | A1 | 9/2013 | Doyle, III et al. |
| 2014/0046159 | A1 | 2/2014 | Kovatchev et al. |
| 2014/0066885 | A1 | 3/2014 | Keenan et al. |
| 2014/0066886 | A1 | 3/2014 | Roy et al. |
| 2014/0066889 | A1 | 3/2014 | Grosman et al. |
| 2014/0066890 | A1 | 3/2014 | Sloan et al. |
| 2014/0114278 | A1 | 4/2014 | Dobbles et al. |
| 2014/0180203 | A1 | 6/2014 | Budiman et al. |
| 2014/0180240 | A1 | 6/2014 | Finan et al. |
| 2014/0200559 | A1 | 7/2014 | Doyle, III et al. |
| 2014/0228743 | A1 | 8/2014 | Budiman |
| 2014/0276554 | A1 | 9/2014 | Finan et al. |
| 2015/0018757 | A1 | 1/2015 | Starkweather et al. |
| 2015/0045767 | A1 | 2/2015 | Kamen et al. |
| 2015/0306312 | A1 | 10/2015 | Palerm |
| 2016/0001002 | A1 | 1/2016 | Yodfat et al. |
| 2017/0348483 | A1* | 12/2017 | Duke .................... A61M 5/142 |
| 2017/0348484 | A1* | 12/2017 | Duke .................... G16H 10/40 |
| 2019/0336684 | A1* | 11/2019 | O'Connor ............. G16H 20/17 |

FOREIGN PATENT DOCUMENTS

| | | |
|---|---|---|
| CN | 105050539 A | 11/2015 |
| JP | 2010-524639 A | 7/2010 |
| JP | 2016-540564 A | 12/2016 |
| WO | WO 2008/134146 A1 | 11/2008 |
| WO | 2012051344 A2 | 4/2012 |
| WO | WO 2014/035570 A2 | 3/2014 |
| WO | WO 2014/110541 A1 | 7/2014 |
| WO | WO 2015/084581 A1 | 6/2015 |
| WO | WO 2016/019192 A1 | 2/2016 |

OTHER PUBLICATIONS

Atlas et al., "MD-Logic Artificial Pancreas System," Diabetes Care, vol. 33, No. 5, May 2010.

Cobelli et al., "Artificial Pancreas: Past, Present, Future" Diabetes vol. 60, Nov. 2011.

Kovatchev et al., "Control to Range for Diabetes: Functionality and Modular Architecture," J. Diabetes Sci. Techn., vol. 3, Issue 5, Sep. 2009.

Lee et al., "A Closed-Loop Artificial Pancreas based on MPC: Human Friendly Identification and Automatic Meal Disturbance Rejection," Proceedings of the 17th World Congress, The International Federation of Automatic Control, Seoul Korea Jul. 6-11, 2008.

Lee et al., "A Closed-Loop Artificial Pancreas Using Model Predictive Control and a Sliding Meal Size Estimator" J. Diabetes Sci. Techn., vol. 3, Issue 5, Sep. 2009.

Magni et al., "Model Predictive Control of Type 1 Diabetes: An in Silico Trial" J. Diabetes Sci. Techn., vol. 1, Issue 6, Nov. 2007.

Magni et al., "Run-to-Run Tuning of Model Predictive Control for Type 1 Diabetes Subjects: In Silico Trial" J. Diabetes Sci. Techn., vol. 3, Issue 5, Sep. 2009.

Soru et al., "MPC Based Artificial Pancreas; Strategies for Individualization and Meal Compensation," Annual Reviews in Control 36, p. 118-128 (2012).

Percival et al., "Closed-Loop Control and Advisory Mode Evaluation of an Artificial Pancreatic Beta Cell: Use of Proportional-Integral-Derivative Equivalent Model-Based Controllers" J. Diabetes Sci. Technol., vol. 2, Issue 4, Jul. 2008.

Percival et al., "Closed-Loop Control of an Artificial Pancreatic β-Cell Using Multi-Parametric Model Predictive Control," Diabetes Res. 2008.

Wang et al., "Automatic Bolus and Adaptive Basal Algorithm for the Artificial Pancreatic β-Cell" Diabetes Techn. Ther., vol. 12, No. 11, 2010.

International Search Report and Written Opinion issued in corresponding International Patent Application No. PCT/US2018/25161, dated Jun. 8, 2018, 10 pages.

Russian Office Action and Search Report for RU 2019134803; dated Feb. 3, 2021; 10 pages.

Japanese Notice of Reasons for Rejection for JP 2019-553969; dated Nov. 30, 2021; 3 pages.

Chinese Office Action for CN 201880035995.1; dated Jan. 6, 2022; 11 pages.

* cited by examiner

MAINTAINING MAXIMUM DOSING LIMITS FOR CLOSED LOOP INSULIN MANAGEMENT SYSTEMS

TECHNICAL FIELD

This invention generally relates to the field of diabetic management systems and more specifically to establishing insulin delivery rate limits for insulin delivery systems.

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, or the presence of an excessive amount of glucose in the blood plasma. Persistent hyperglycemia alone or in combination with hypoinsulinemia is associated with a variety of serious symptoms and life threatening long term complications. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

Substantial improvements in diabetes therapy have been achieved by the development of drug delivery devices that relieve the patient of the need for syringes or drug pens for the administration of multiple daily injections. These drug delivery devices allow for the delivery of the drug in a manner that bears greater similarity to the naturally occurring physiological processes and can be controlled to follow a standard of individually modified protocols to give the patient better glycemic control.

These drug delivery devices can be constructed as implantable devices. Alternatively, the delivery device may be an external device with an infusion set for subcutaneous infusion to the patient via the transcutaneous insertion of a catheter, cannula, or transdermal drug transport, such as through a patch. The external drug delivery device may be mounted on clothing or, and more preferably, hidden beneath or inside clothing, or mounted on the body and are generally controlled via a user interface built-in to the device or on a separate remote device.

Blood or interstitial glucose monitoring is required to achieve acceptable glycemic control with the devices. For example, delivery of suitable amounts of insulin by the drug delivery device requires that the patient frequently determines his or her blood glucose level. The level value may be input into the delivery device, or pump, or on a controller, after which suitable modification may be calculated to the default, or currently in-use, insulin delivery profile, i.e., dosage and timing, which modification is used to adjust the drug delivery device operation accordingly. Alternatively, or in conjunction with episodic blood glucose determination, continuous glucose monitoring ("CGM") may be used with the drug delivery devices. CGM allows for closed-loop control of the insulin being infused into the diabetic patient.

To allow for closed-loop control, autonomous modulation of the drug being delivered to the user is provided by a controller using one or more algorithms. For example, proportional-integral-derivative algorithms ("PID") that are reactive to observed glucose levels may be utilized, which algorithms can be tuned based on rules of the mathematical models of the metabolic interactions between glucose and insulin in a person. Alternatively, a model predictive control algorithm ("MPC") may be used. The MPC is advantageous because the MPC proactively considers the near future effects of control changes, sometimes subject to constraints, in determining the output of the MPC, whereas PID typically involves only past outputs in determining future changes. Constraints can be implemented in the MPC controller such that a solution in a confined "space," e.g., within imposed delivery limitations, is guaranteed and the system is prevented from exceeding a limit that has been reached.

Known MPCs are described in the following documents: U.S. Pat. No. 7,060,059; U.S. Patent Application Nos. 2011/0313680, 2011/0257627, and 2014/0180240; International Publication WO 2012/051344, Percival et al., "*Closed-Loop Control and Advisory Mode Evaluation of an Artificial Pancreatic Beta Cell: Use of Proportional-Integral-Derivative Equivalent Model-Based Controllers*" J. Diabetes Sci. Technol., Vol. 2, Issue 4, July 2008; Paola Soru et al., "*MPC Based Artificial Pancreas; Strategies for Individualization and Meal Compensation*," Annual Reviews in Control 36, p. 118-128 (2012); Cobelli et al., "*Artificial Pancreas: Past, Present, Future*" Diabetes Vol. 60, November 2011; Magni et al., "*Run-to-Run Tuning of Model Predictive Control for Type 1 Diabetes Subjects: In Silico Trial*" J. Diabetes Sci. Techn., Vol. 3, Issue 5, September 2009; Lee et al., "*A Closed-Loop Artificial Pancreas Using Model Predictive Control and a Sliding Meal Size Estimator*" J. Diabetes Sci. Techn., Vol. 3, Issue 5, September 2009; Lee et al., "*A Closed-Loop Artificial Pancreas based on MPC: Human Friendly Identification and Automatic Meal Disturbance Rejection*," Proceedings of the 17$^{th}$ World Congress, The International Federation of Automatic Control, Seoul Korea Jul. 6-11, 2008; Magni et al., "*Model Predictive Control of Type 1 Diabetes: An in Silico Trial*" J. Diabetes Sci. Techn., Vol. 1, Issue 6, November 2007; Wang et al., "*Automatic Bolus and Adaptive Basal Algorithm for the Artificial Pancreatic β-Cell*" Diabetes Techn. Ther., Vol. 12, No. 11, 2010; Percival et al., "*Closed-Loop Control of an Artificial Pancreatic β-Cell Using Multi-Parametric Model Predictive Control*," Diabetes Res. 2008; Kovatchev et al., "*Control to Range for Diabetes: Functionality and Modular Architecture*," J. Diabetes Sci. Techn., Vol. 3, Issue 5, September 2009; and Atlas et al., "*MD-Logic Artificial Pancreas System*," Diabetes Care, Vol. 33, No. 5, May 2010. All articles or documents cited in this application are hereby incorporated by reference into this application as if fully set forth herein.

Typically, an MPC constraint is a constant maximum value arbitrarily chosen or determined based solely on the basal delivery rate. However, such a static constraint fails to account for the effects of temporary basal rates and extended boluses or extended portions of combination boluses. If this constraint results in aggressive control, over-insulinization and hypoglycemia will result, while overly conservative constraints may result in ineffective control. Thus, there is a need for intelligent constraints on insulin delivery output.

DETAILED DESCRIPTION

The discovery of the invention is a technique that allows a controller to determine a dynamic constraint for insulin dosing in a diabetes management system, such as, for example, an artificial pancreas. This dynamic constraint is determined in view of basal delivery rates, temporary delivery rates, and extended boluses. Advantageously and according to at least one version, insulin delivery can proceed safely without adversely affecting the effectiveness of the diabetes management system.

According to a first aspect, a method for determining a maximum insulin delivery rate for a closed loop insulin management system is described. The system includes a continuous glucose monitor configured to continuously measure the glucose level of a subject at discrete, generally (when no glucose data is lost) uniform time intervals and provide the glucose level at each interval in the form of glucose measurement data. The system additionally includes an insulin infusion pump to deliver insulin, and a controller operatively coupled to the pump and continuous glucose monitor. The method includes determining, via a processor, if a temporary basal insulin delivery rate is applied or delivered to the user by the controller. The method further includes mapping the temporary basal insulin delivery rate to determine the maximum insulin delivery rate when the temporary basal insulin delivery rate is applied and mapping a basal insulin delivery rate to determine the maximum insulin delivery rate when no temporary basal insulin delivery rate is applied.

In an example, mapping the temporary basal insulin delivery rate includes increasing the resulting total basal insulin delivery rate to a predetermined percentage to determine the maximum insulin delivery rate. In another example, mapping the default basal insulin delivery rate includes increasing the default basal insulin delivery rate to a predetermined percentage to determine the maximum insulin delivery rate. The controller can use a model predictive control algorithm ("MPC") and the mapping may be carried out by a sub-controller, the sub-controller being an algorithm controller. In another embodiment, the controller may use a PID control algorithm. The method can further include determining, via a processor, if an extended bolus is active. The method further includes increasing, via the controller, the determined maximum insulin delivery rate by a value of the extended bolus when the extended bolus is active and making no change to the determined maximum insulin delivery rate when no extended bolus is active. The method additionally includes determining, via the processor, if the temporary basal insulin delivery rate is a negative value. The method includes mapping the total basal insulin delivery rate when the temporary basal insulin delivery rate is a negative value and disregarding the temporary insulin delivery rate and mapping the default basal insulin delivery rate when the temporary basal insulin delivery rate is a positive value. In an example, the maximum insulin delivery rate is 300% of the basal rate. In an example, the percentage increase is a constant.

According to another aspect, a method for determining a maximum insulin delivery rate for an insulin delivery system is described. The system includes a continuous glucose monitor, an insulin infusion pump, and a blood glucose monitor. The method includes increasing the basal insulin delivery rate to a predetermined percentage to determine the maximum insulin delivery rate.

In an embodiment, the method further includes determining, via the processor, when an extended bolus is active and increasing, via the controller, the determined maximum insulin delivery rate by the value of the extended bolus when the extended bolus is active. The method can further include determining, via the processor, if a temporary basal insulin delivery rate is applied. When the temporary basal insulin delivery rate is applied, the method can include determining via the processor if the temporary basal insulin delivery rate is a negative value. When the temporary basal insulin delivery rate is a negative value, the method can include increasing the resulting total basal insulin delivery rate to the predetermined percentage to determine the maximum insulin delivery rate. When the temporary insulin delivery rate is a positive value, the method can further include increasing the default basal insulin delivery rate, which is not affected by the positive temporary basal rate, to the predetermined percentage to determine the maximum insulin delivery rate.

According to yet another aspect, a system for management of diabetes is described. The system includes a continuous glucose monitor, an insulin infusion pump to deliver insulin, and a controller operatively coupled to the pump and blood glucose monitor. The controller is configured to use a control algorithm to predict at least one future glucose value based on, among other things, prior glucose measurement data from the continuous glucose monitor and to determine a maximum insulin delivery rate for the insulin infusion pump at a current time interval based on a basal insulin delivery rate, a temporary basal insulin delivery rate, an extended bolus, or a combination thereof.

As used herein, the terms "patient," "user," and "subject," refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include pharmaceuticals or other chemicals that cause a biological response in the body of a user or patient and preferably is insulin.

Figure 1:
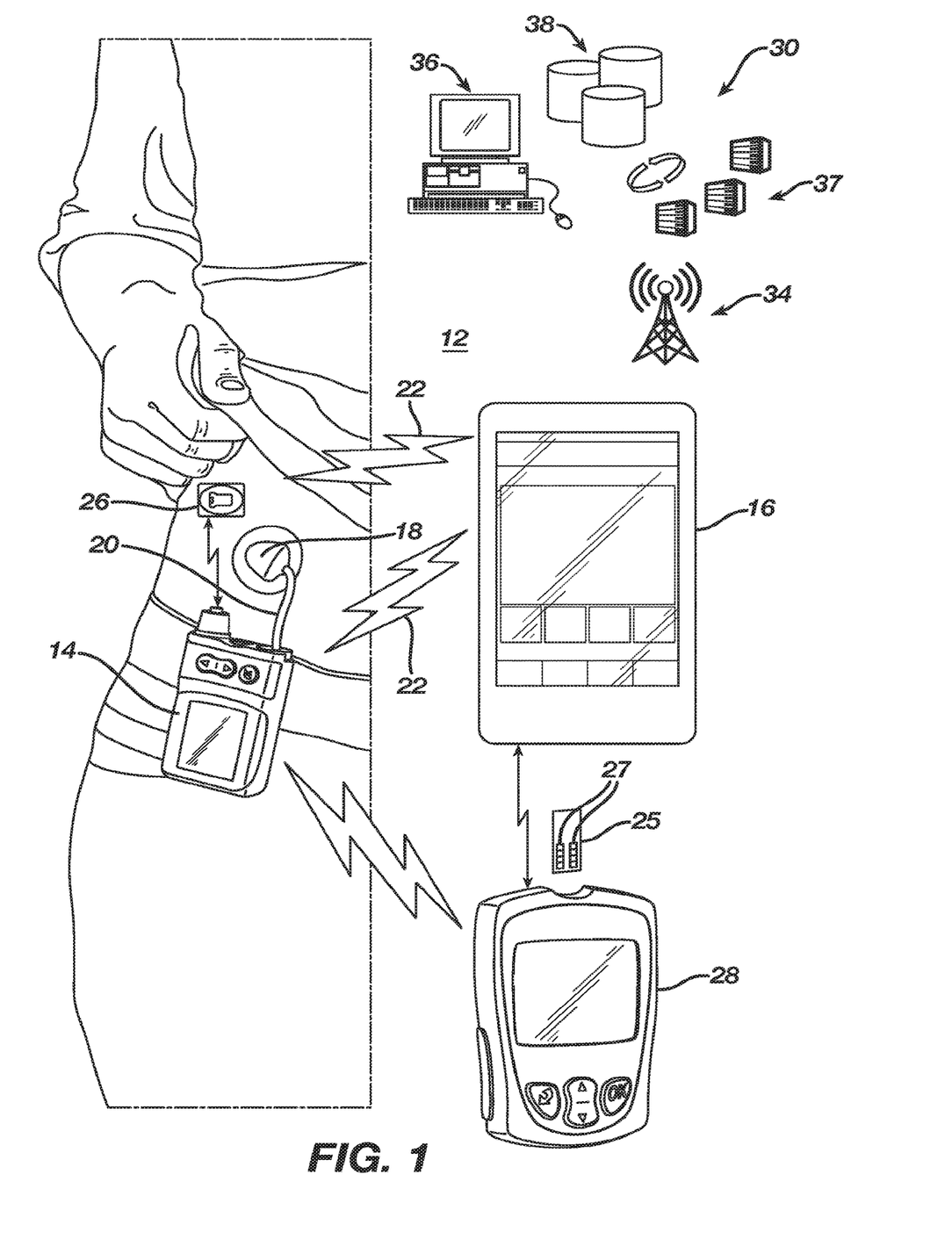
FIG. 1 illustrates an embodiment of a diabetes management system.

FIG. 1 illustrates a diabetes management system 12 according to an embodiment that utilizes the principles of the invention. The system 12 includes a drug delivery device 14. In an embodiment, the drug delivery system 12 also includes a remote controller 16. The drug delivery device 14 is connected to an infusion set 18 via flexible tubing 20.

The drug delivery device 14 is configured to transmit and receive data to and from the controller 16 by, for example, a communications link 22 such as radio frequency ("RF"), Bluetooth® or the like. In one embodiment, the drug delivery device 14 is an insulin infusion device, or pump, and the controller 16 may be a hand-held portable controller, or a consumer electronic device, such as a smart phone, computer, exercise or user monitoring device, or the like. In such an embodiment, data transmitted from the drug delivery device 14 to the controller 16 may include information such as, for example, insulin delivery data, blood glucose information, basal, bolus, insulin to carbohydrates ratio, insulin sensitivity factor, and the like. The controller 16 can be configured to include a closed-loop controller that has been programmed to receive continuous glucose readings from a CGM sensor 26 via a communications link 22. Data transmitted from the controller 16 to the drug delivery device 14 may include glucose test results and a food database to allow the drug delivery device 14 to calculate the amount of insulin to be delivered. Alternatively, the controller 16 may perform basal dosing or bolus calculation and send the results of such calculations to the drug delivery device for delivery of insulin. Bolus calculation may be done manually upon initiation by the subject, or may be automated so that the system is capable of incorporation both bolus and basal insulin control.

A glucose meter 28 (e.g., an episodic blood glucose meter), alone or in conjunction with the CGM sensor 26, provides data to either of or both the controller 16 and drug delivery device 14, e.g., via a communications link. The glucose meter 28 can measure a fluid sample placed on a test strip 25. The two hatched areas 27 on the test strip 25 graphically represent two electrodes. The controller 16 can present information and receive commands via a user interface such as a touchscreen, or other devices, and as discussed below with reference to a user interface 60 of FIG. 2.

The controller 16, the drug-delivery device 14, and the CGM sensor 26 can be integrated into multi-function units in any combination. For example, the controller 16 can be integrated with the drug-delivery device 14 to form a combined device with a single housing. Infusion, sensing, and controlling functions can also be integrated into a monolithic artificial pancreas. In various embodiments, the controller 16 is combined with the glucose meter 28 into an integrated monolithic device having a housing 32. Such an integrated monolithic device can receive a test strip 25. In other embodiments, the controller 16 and the glucose meter 28 are two separable devices that are dockable with each other to form an integrated device. Each of the devices 14, 16, and 28 has a suitable micro-processor (not shown for brevity) programmed to carry out various functionalities.

The drug delivery device 14 or the controller 16 can also be configured for bi-directional communication with a remote health monitoring station 30 through, for example, a communication network 34. One or more servers 37 or storage devices 38 can be communicatively connected to the controller 16 via the network 34. In an example, the drug delivery device 14 communicates with a personal computer (36) via a communication link, such as RF, Bluetooth®, or the like. The controller 16 and the remote station 30 also can be configured for bi-directional wired communication through, for example, a telephone land based communication network. Examples of remote monitoring stations 30 may include, but are not limited to, a personal or networked computer 36, a server 38 to a memory storage, a personal digital assistant, other mobile telephone, a hospital base monitoring station or a dedicated remote clinical monitoring station. Alternatively and though not shown in FIG. 1, storage for, for example, the control algorithm, may further be provided in the cloud.

The control algorithm can reside in the remote controller 16, in the drug delivery device 14, or both in the configurations shown in FIG. 1. In one configuration, the controller 16 will wirelessly gather the necessary information (e.g., insulin history) from the drug delivery device 14, as well as from the glucose sensor 26 (e.g., glucose data) to allow the drug delivery device 14, using the control algorithm, to calculate the amount of insulin to be modulatively delivered by the drug delivery device 14. Alternatively, the controller 16 includes the control algorithm and may perform basal dosing or bolus calculation and send the results of such calculations along with delivery instructions to the drug delivery device 14. In an alternative embodiment, an episodic blood glucose meter 28 and biosensors 25 also may be used alone or in conjunction with the CGM sensor 26 to provide blood glucose data to either of or both the controller 16 and the drug delivery device 14.

Figure 2:
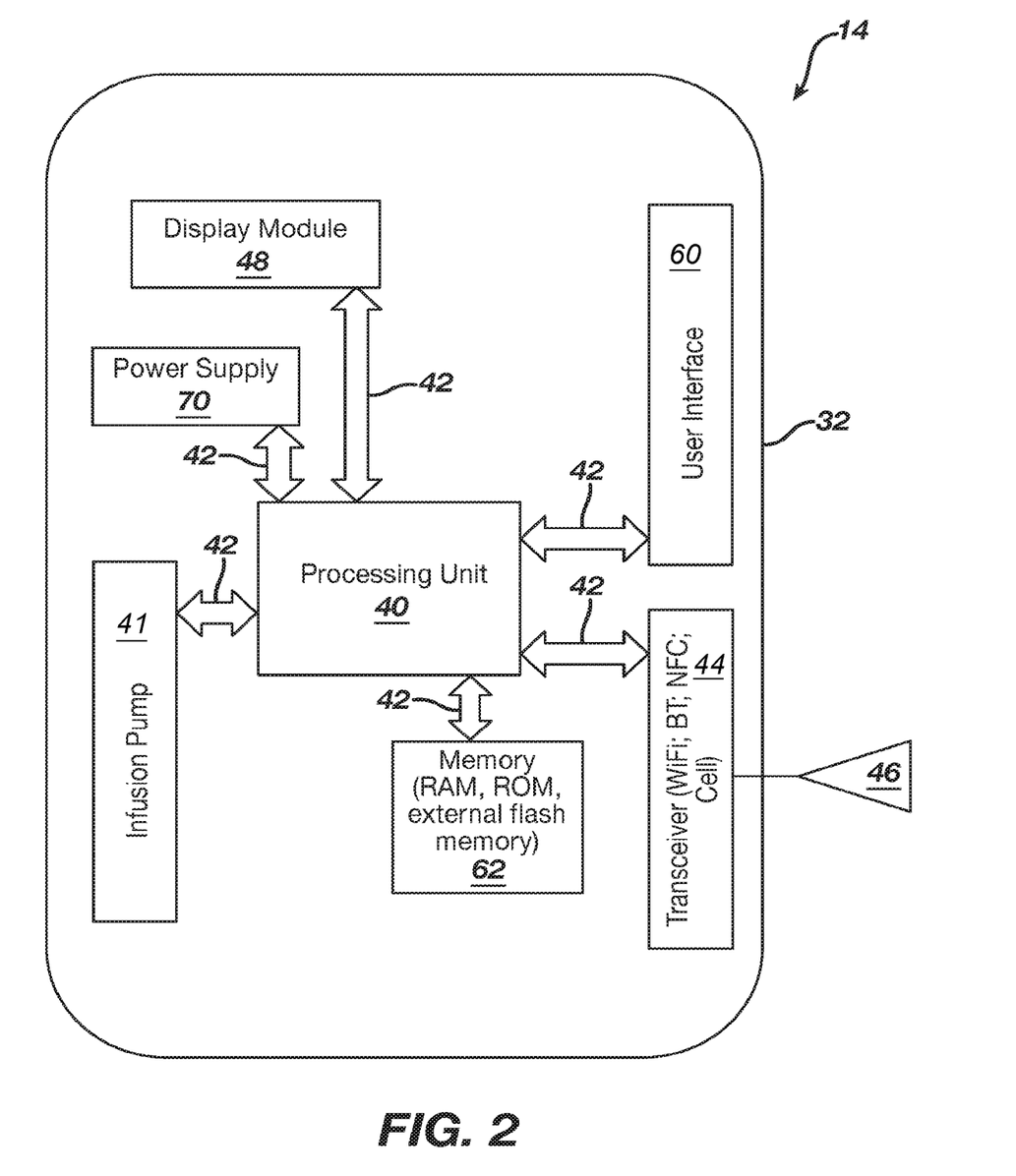
FIG. 2 illustrates the components for a drug delivery device used in the system of FIG. 1.

Referring to FIG. 2, the drug delivery device 14 includes a drug delivery mechanism or infusion pump 41 (e.g., an insulin pump and drive mechanism) for forcing insulin from an insulin reservoir (e.g., an insulin cartridge) through a side port connected to an infusion set (18 and 20 of FIG. 1) and into the body of the user. The drug delivery device 14 may include interface buttons and the buttons may be mechanical or electrical switches; however, a touch screen interface with virtual buttons also may be utilized. The electronic components of the drug delivery device 14 can be disposed on, for example, a printed circuit board situated within a housing 32 and forming the drug delivery device 14 described herein. FIG. 2 illustrates, in simplified schematic form, several of the electronic components disposed within the housing 32 for purposes of this embodiment. The drug delivery device 14 includes a processing unit 40 in the form of a microprocessor, a microcontroller, an application specific integrated circuit ("ASIC"), a mixed signal processor ("MSP"), a field programmable gate array ("FPGA"), or a combination thereof, and is electrically connected to various electronic modules included on, or connected to, the printed circuit board, as will be described below. The processing unit 40 is electrically connected to, for example, a transceiver circuit of a wireless module 44 over a communication path 42, the transceiver circuit being connected to an antenna 46, that receives the aforementioned transmitted glucose measurement information from the glucose sensor.

A display module 48, that may include a display processor and display buffer, is electrically connected to the processing unit 40 over the communication path 42 for receiving and displaying output data as described above, and for displaying user interface input options under control of processing unit 40. Although not shown in FIG. 2, the processing unit 40 has electrical access to a digital time-of-day clock connected to the printed circuit board for recording dates and times of periodic glucose measurements received from the glucose sensor, which may then be accessed, uploaded, or displayed as necessary. Associated with the clock is a timer for recording elapsed times, preset or predetermined time delays under programmed control of the processing unit 40.

A memory module 62, that includes, but is not limited to, volatile random access memory ("RAM"), a non-volatile memory, which may comprise read-only memory ("ROM") or flash memory, and a circuit for connecting to an external portable memory device port, is electrically connected to the processing unit 40 over a communication path 42. External memory devices may include flash memory devices housed in thumb drives, portable hard disk drives, data cards, or any other form of electronic storage devices. The on-board memory can include various embedded and default applications executed by the processing unit 40 for operation of the handheld communication unit 16, as will be explained below. On-board memory can also be used to store a history of a user's glucose measurements including dates and times associated therewith. Using the wireless transmission capability of the drug delivery device 14, as described below, such measurement data can be transferred via wired or wireless transmission to connected computers or other processing devices.

A wireless module 44 may include transceiver circuits for wireless digital data transmission and reception via one or more digital antennas 46, and is electrically connected to the processing unit 40 over the communication path 42. The wireless transceiver circuits may be in the form of integrated circuit chips, chipsets, programmable functions operable via processing unit 40, or a combination thereof. Each of the wireless transceiver circuits may be compatible with a different wireless transmission standard, for example, the Wireless Local Area Network IEEE 802.11 ("WiFi"), Bluetooth®, or other RF transimission standards, near field communication ("NFC"), and the like. The wireless transceiver circuit may also be configured to receive and process data transmitted over a preselected communication channel from the glucose sensor worn by the user. Yet as another alternative, the wireless transceiver circuit may be a circuit for cellular communication with cellular networks and be configured to detect and link to available cellular communication towers.

A power supply module 70 is electrically connected to all modules in the housing 32 and to the processing unit 40 to supply electric power thereto. The power supply module 70 may comprise standard or rechargeable batteries or an AC/DC power supply which may be activated when the drug delivery device 14 is connected to a source of AC/DC power. The power supply module 70 is also electrically connected to the processing unit 40 over the communication path 42 such that processing unit 40 can monitor a power level remaining in the battery power module of the power supply module 70.

Glucose levels or concentrations can be determined by the use of the CGM sensor. The CGM sensor utilizes amperometric electrochemical sensor technology to measure glucose with three electrodes (not shown) operably connected to the sensor electronics and covered by a sensing membrane and a bio-interface membrane, which are attached by a clip.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the species being measured at the working electrode. In the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of glucose in the interstitial fluid, and therefore may be utilized to estimate a meaningful blood glucose value. Details of a suitable sensor and associated components are shown and described in U.S. Pat. No. 7,276,029, which is incorporated by reference herein as if fully set forth here in this application. In one embodiment, a continuous glucose sensor from the Dexcom, Inc. such as the G4® or G5® system can also be utilized with the exemplary embodiments described herein.

Figure 3:
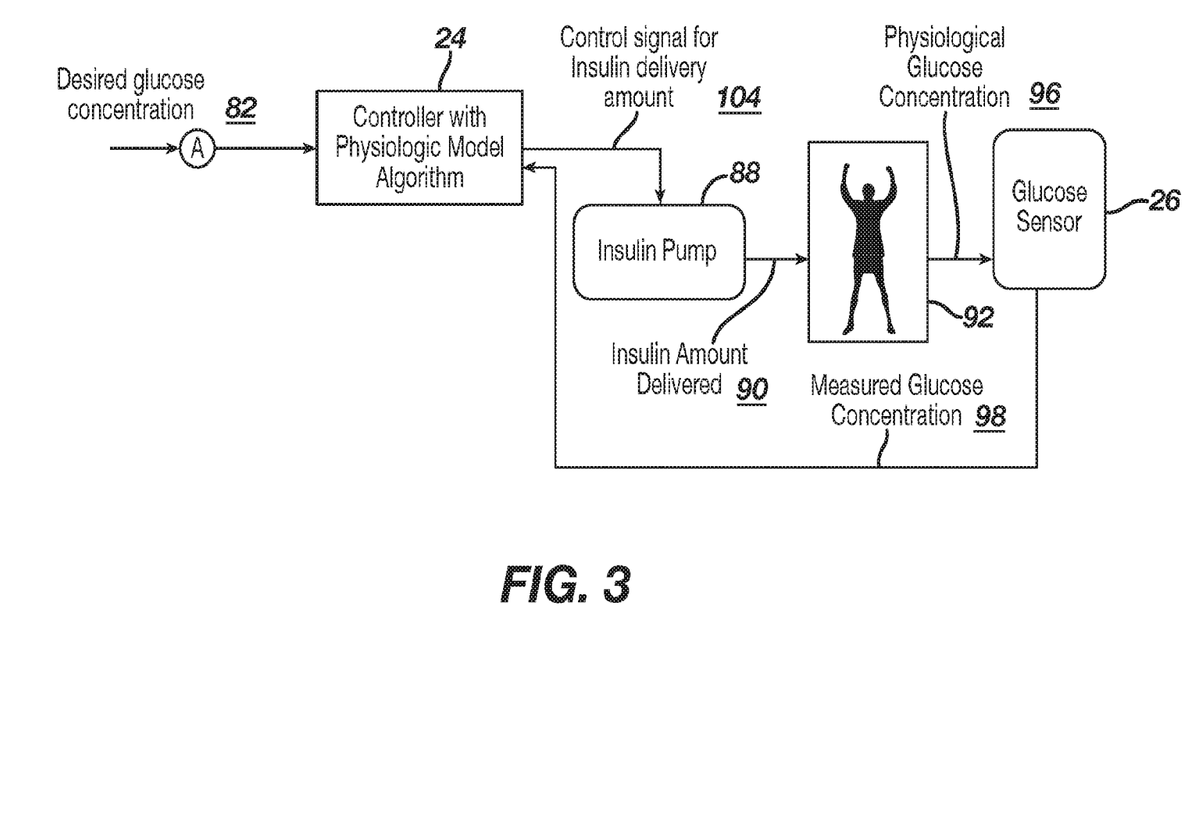
FIG. 3 illustrates an embodiment of the diabetes management system of FIG. 1 in schematic form.

FIG. 3 illustrates a schematic diagram 80 of an embodiment of the system in FIG. 1. In particular, FIG. 3 provides for an WC programmed into a control logic module 24 that is utilized in the remote controller 16. The WC enabled module 24 receives a desired glucose concentration or range of glucose concentrations 82.

Referring to FIG. 3, the first output of the MPC-enabled control logic 24 can be a control signal 104 to an insulin pump 88 of a drug delivery device 14 to deliver a desired quantity of insulin 90 into the subject 92 at predetermined time intervals, which, for example, can be indexed every 5 minutes. A glucose sensor 26 measures the actual glucose levels 96 in the subject 92 in order to provide the measured glucose levels 98 to the control algorithm.

The drug delivery device, according to a preferred embodiment, houses a pump delivery module, CGM module and an MPC module. Preferably, this embodiment employs a hypoglycemia-hyperglycemia minimizer ("HHM") system as, for example, disclosed in U.S. Pat. No. 8,526,587 and U.S. patent application Ser. No. 14/015,831, both of which are incorporated in their entireties herein by reference, each being integrated within the housing of the drug delivery device. The CGM module is configured for receiving signals from a CGM sensor, placed on the patient. The MPC module is operatively connected to the CGM module as well as the pump delivery module and is configured to receive subcutaneous glucose information for providing the same to a stored algorithm, which is also made aware of all previous deliveries of insulin. These data are used to calculate near-future predictions of glucose levels and produce an insulin delivery rate that would mitigate the near-future predicted, or actual, hyper or hypoglycemic conditions. The rate is then actuated by the pump delivery module relative to the patient set rate corresponding to the current (e.g., 5 minute) interval. This protocol is repeated for each subsequent time interval.

Exemplary algorithms for use in the MPC module are detailed in U.S. Pat. Nos. 8,562,587 and 8,762,070 and U.S. application Ser. Nos. 13/854,963 and 14/154,241, the entire contents of which are herein incorporated by reference, creating predictive values for controlling the delivery of insulin based on basal rate, meal activities and continuous glucose monitoring. As noted above, insulin is delivered to the patient in this embodiment and for all following portions of this discussion using the HHM system. However and as noted previously, other known MPC or PID type delivery systems and predictive algorithms employed thereby can be utilized.

Rules or constraints for insulin delivery for the diabetes management system of the invention are devised and instituted to minimize safety risks while maximizing the efficacy of the dosing, or control, algorithm. When the patient's CGM indicates a hypoglycemic event, or such an event is predicted by the control algorithm, the controller will withhold part or all of the patient-scheduled insulin delivery amount in order to mitigate, if not avoid, the hypoglycemic event. The algorithm is permitted to withhold up to 100 percent of any patient-scheduled insulin delivery amount in order to mitigate an actual or predicted hypoglycemic excursion. This patient-scheduled insulin delivery amount includes a basal amount and may include a temporary basal amount, as well as the extended bolus.

When the patient's CGM 26 indicates a hyperglycemic event or such an event is predicted by the control algorithm, the controller will increase insulin delivery above the patient-scheduled insulin delivery amount in order to mitigate, if not avoid, the hyperglycemic event. To keep this increase safe yet effective, the algorithm has specific limits, i.e., a maximum, on how much insulin above the patient-scheduled insulin delivery amount can be delivered.

Figure 4:
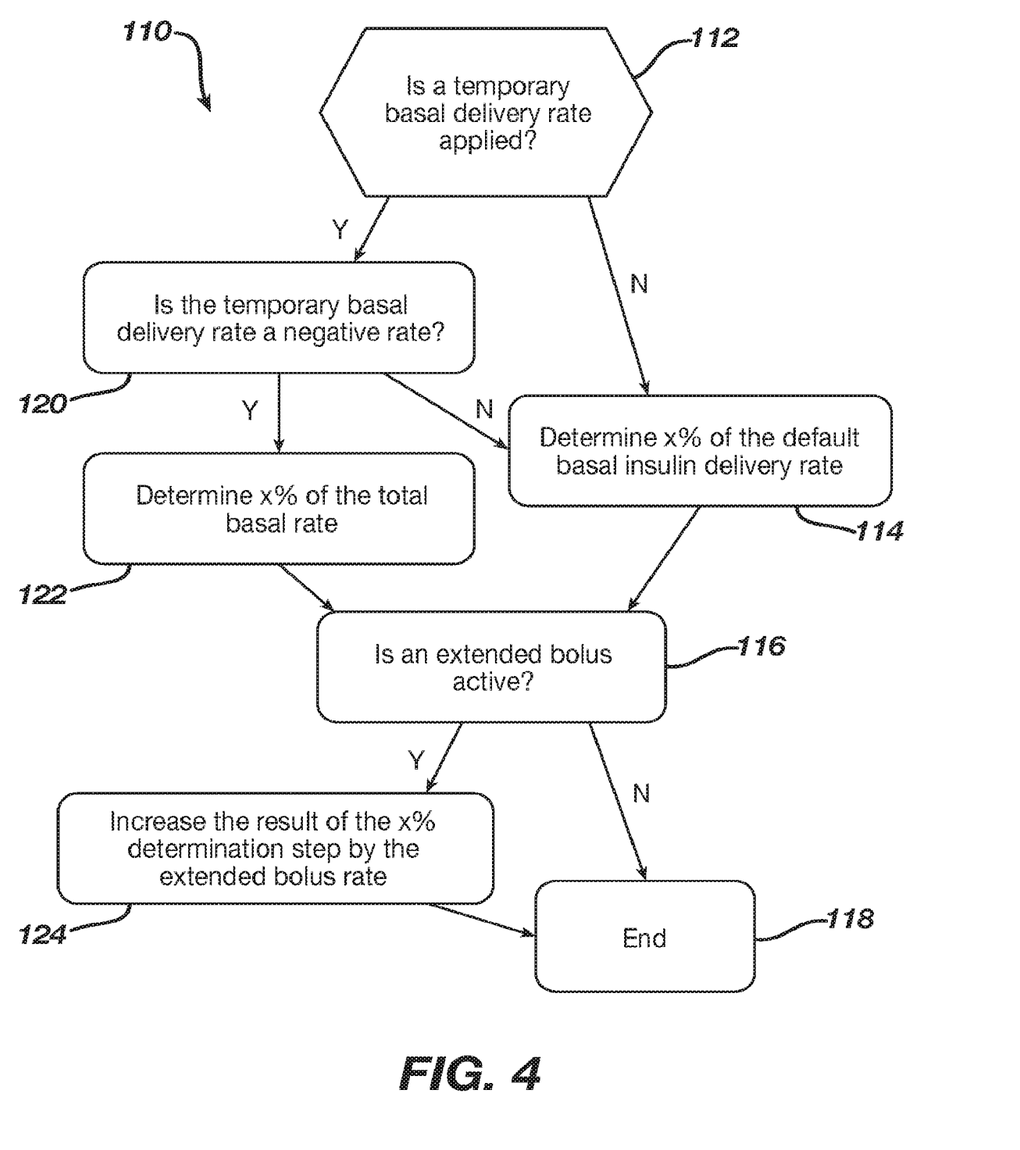
FIG. 4 is a flow diagram illustrating an embodiment of a method for determining a maximum insulin delivery rate.

FIG. 4 presents a flow or process diagram illustrating an embodiment of a method 110 for determining a maximum insulin delivery rate. In this embodiment, the method employs an algorithm that takes into account basal delivery rate, and may include a temporary basal delivery rate and an extended bolus if they are applied by the user. In this embodiment, the MPC controller 24 includes several sub-controllers, such as master, algorithm, and CGM controllers. Upon entry by the user, a basal rate, temporary basal rate, and an extended bolus are saved in memory by the master controller and used by the algorithm controller in calculations, such as in calculating a maximum insulin delivery rate. In an example, the controller calculates the maximum insulin delivery rate at predetermined time intervals (e.g., every five (5) minutes).

Returning to FIG. 4, the method begins at block 112 when the processor determines if a temporary basal delivery rate is applied. If no temporary basal delivery rate has been applied, at block 114 the processor maps the default basal rate, i.e., the basal rate originally scheduled by the user, with no temporary basal rate nor extended bolus applied, to determine the maximum insulin delivery rate. In this embodiment, the processor determines the maximum insulin delivery rate to be x % of the default basal rate. In one embodiment, the maximum insulin delivery rate is set as 300% of the default basal rate. The percentage increase of the basal rate can be determined using simulations, determined adaptively, such as based on a learning algorithm, or input by a patient or health care professional, among other methods. In this embodiment, the percentage increase is fixed. In other embodiments, the percentage increase may vary depending on time of day or other factors, such as exercise, illness, and patient or caregiver preference. For example, the percentage increase to 300% can be set to determine the maximum delivery rate during the overnight period to err on the side of safety when the patient is asleep and therefore might not be aware of potential hypoglycemia.

At block 116, the processor determines if an extended bolus is active. If no extended bolus is active, the method ends at block 118 and the maximum insulin delivery rate is set as x % of the default basal rate. If an extended bolus is active, at block 124 the processor increases the maximum delivery rate of x % multiplied by the default basal rate by the value of the extended bolus rate and the method ends at block 118 with the maximum insulin delivery rate determined as:

maximum rate=($x$% of default basal rate)+extended bolus rate.

Extended boluses are typically employed to handle carb-related events, such as a slow-absorbing meal or a "grazing" session. In order to conservatively deal with these carb-related events, the controller is only able to withhold insulin from the extended bolus. The controller cannot deliver more insulin than requested in order to safeguard against over-insulinization and the resulting hypoglycemia. Thus, the percentage increase is never applied to the extended bolus amount.

Returning to block 112, if a temporary basal delivery rate is applied, at block 120 the processor determines if the temporary basal delivery rate is a negative rate, meaning that the delivery rate for the total basal rate is less than the delivery rate for the default basal rate. If the temporary basal delivery rate is a positive value, the processor disregards the temporary basal delivery rate, i.e., default basal rate=total basal rate, and the method moves to block 114. If the temporary basal delivery rate is a negative rate, the maximum delivery rate is determined as x % of the resulting total basal rate (e.g., maximum rate=x % of (default basal rate+temporary basal rate). Following this calculation, the method moves to block 116 and determines if an extended bolus is applied.

Basal delivery rate adjustments are typically employed when addressing systemic temporary metabolic fluctuations such as exercise or illness and are typically not directly tied to carb-related events. Thus, adjustments to the basal delivery rate, in the form of temporary basal delivery rate, can be factored into the controller's insulin-delivery target. With a negative temporary basal rate, the system is more conservative than with an applied default basal delivery rate. Thus, the percentage increase is applied when the negative temporary basal rate is applied. With a positive temporary basal delivery rate, on the other hand, the system is already more aggressive and the percentage increase is not applied to the applied positive temporary basal delivery. By applying the percentage increase to the default basal delivery rate when a positive temporary basal rate is applied, rather than applying the percentage increase to the applied positive temporary basal rate, the controller more robustly safeguards against over-insulinization.

Two alternatives to the above described method are (i) basing the controller's maximum insulin delivery entirely on the effective total insulin delivery rate, inclusive of temporary basal rates and extended bolus; and (ii) basing the controller's maximum insulin delivery on temporary basal rates equally, whether positive or negative, but not on extended boluses. The first situation (i) is overly aggressive because the percentage increase may be applied to already high rates due to a positive temporary basal rate or an extended bolus. The second situation (ii) is also overly aggressive because the percentage increase may again be applied to already high rates.

As illustrated above, the maximum insulin delivery rate is determined as either x % of the default basal rate (the degenerate case of the total basal rate), x % of the default basal rate plus the extended bolus rate (a total basal rate of such certain composition), or x % of the default basal rate plus temporary basal rate (when a negative temporary basal rate is applied—another composition of total basal rate), or x % of the default basal rate plus temporary basal rate (when a negative temporary basal rate is applied) plus the extended bolus rate (yet another way of composing the total basal rate). In an example, the algorithm to calculate the maximum insulin delivery rate is invoked every five minutes.

While determination of the maximum insulin delivery rate has been described above in the context of a constant or fixed percentage, in other embodiments the percentage may be adjustable based on various factors, such as patient or health care professional preference, the time of day, and an adaptive learning system, among others. In addition, the percentage may also be adjustable based on different modes of operation, such as an overnight mode or an exercise mode. In addition, differing percentages may be used based on which type of rate, i.e., default basal rate vs. temporary basal rate, is applied and whether an extended bolus is active. Further, while the maximum insulin delivery rate has been described above as being independent of the positive temporary basal rate, in an alternative embodiment, the maximum insulin delivery rate can be determined based on the positive temporary basal rate. For example, a smaller percentage can be used to calculate the maximum insulin delivery rate based on the positive temporary basal rate, as compared to the percentage used to calculate the maximum insulin delivery rate based on the default basal insulin delivery rate.

The determined maximum insulin delivery rate is saved in memory 62 and limits the maximum amount of insulin deliverable by the insulin pump 88 to the determined maximum insulin delivery rate. The insulin pump 88 has a hard limit on how much insulin the insulin pump 88 is able to deliver. Implementation of the determined maximum insulin delivery rate cannot exceed this hard limit.

Figure 5A:
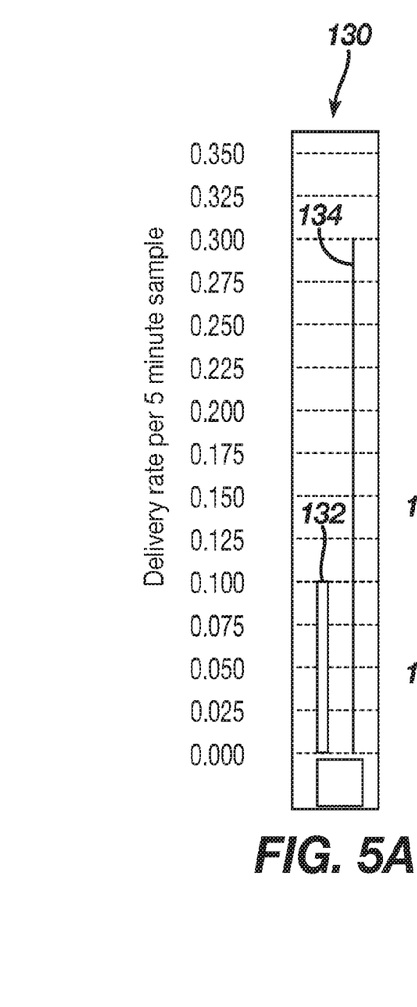
FIGS. 5A-5F illustrate example scenarios for calculating a maximum insulin delivery rate using the method of the invention.

Referring to FIGS. 5A-5F, illustrated are various example scenarios for calculating the maximum insulin delivery rate. In these examples, the delivery rates are illustrated as per 5 minute samples and the x %=300%, e.g., the maximum insulin delivery rate is calculated as 300% of the basal rate. FIG. 5A illustrates an example 130 in which only a basal delivery rate 132 is active. In this example, the basal delivery rate 132 is 1.2 U/hr, which is equivalent to 0.1 U/5-minute sample as illustrated in FIG. 5A. In this example 300% of the basal delivery rate 132 results in a maximum insulin delivery rate 134 of 0.3 U per 5-minute sample, as illustrated in FIG. 5A. Referring to the alternative situations described above, neither alternative situation is applicable with regard to this example.

Figure 5B:
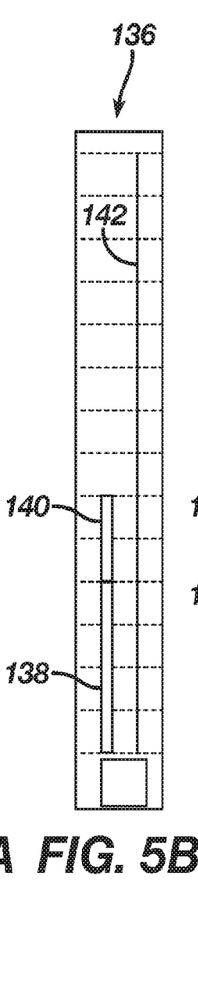

FIG. 5B illustrates an example 136 in which the extended bolus 140 is active in addition to the basal rate 138. In this example, the basal rate 138 is 1.2 U/hr, which is equivalent to 0.1 U/5-minute sample, and the extended bolus 140 is 1.8 U over 3 hours, which is equivalent to 0.05 U per 5-minute sample. In this example, the maximum delivery amount 142 is calculated as[(300% of basal rate)+extended bolus rate]= [(300% of 0.1)+0.05]=0.35 U per 5-minute sample, as illustrated in FIG. 5B. Referring to the above described alternatives, using alternative (i), the maximum delivery amount 142 would be calculated as (300% of total programmed delivery)=(300% of 0.15)=0.45U per 5-minute sample. Such a maximum delivery is overly aggressive and can result in hypoglycemia.

Figure 5C:
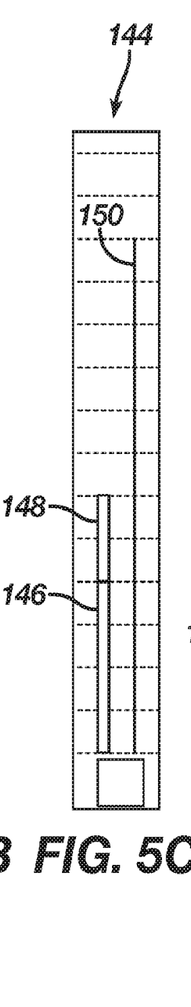

FIG. 5C illustrates an example 144 in which a positive temporary basal rate 148 is applied. The maximum insulin delivery rate 150 is independent of the positive temporary basal rate 148. Thus, the temporary basal rate 148 is disregarded and the maximum insulin delivery rate 150 is calculated based on the basal rate 146, as illustrated in FIG. 5A. In this example, the basal delivery rate 146 is 1.2 U/hr, which is equivalent to 0.1 U/5-minute sample, and the maximum insulin delivery rate 150 is determined as 300% of the basal delivery rate 146. Thus, in this example, the maximum insulin delivery rate 150 is determined to be 0.3 U per 5-minute sample, as illustrated in FIG. 5C. Referring to the above described alternatives, using alternative (i) or (ii), the maximum delivery amount is calculated as (300% of total programmed delivery)=(300% of 0.15)=0.45U per 5-minute sample. Again, such a maximum delivery is overly aggressive and can result in hypoglycemia.

Figure 5D:
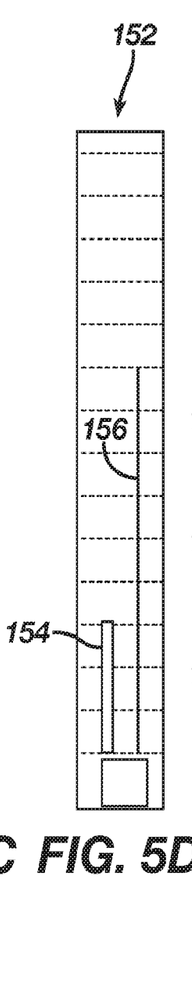

FIG. 5D illustrates an example 152 in which a negative temporary basal rate is applied. In this example, the default basal rate is reduced by the delta of the negative temporary basal rate, resulting in a total basal rate 154. In this example, with a default basal rate of 1.2 U/hr (0.1 U/5-minute sample) and a delta negative temporary basal rate of −25%, the resulting total basal rate 154 is 0.9 U/hr, which is equivalent to 0.075 U/5-minute sample. The maximum insulin delivery rate 156 is calculated as [300% of total basal rate=300% of 0.075=0.225 U per 5-minute sample]. Neither alternative discussed above is applicable in this situation.

Figure 5E:
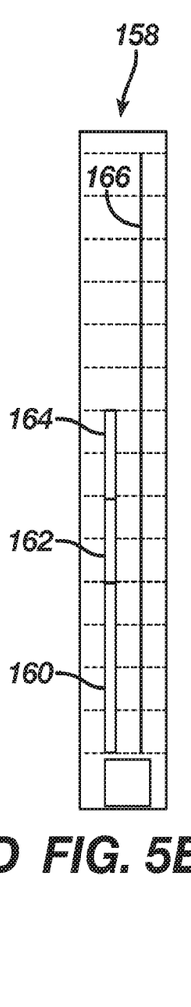

FIG. 5E illustrates an example 158 in which both a positive temporary basal rate 162 is applied and an extended bolus 164 is active. In this example, the maximum delivery amount 166 is calculated in view of the extended bolus rate 164, but independent of the positive temporary basal rate 162 in order to safeguard against over-insulinization. In this example, the basal rate 160 is 1.2 U/hr (0.1 U/5-minute sample) and the extended bolus amount 164 is 1.8 U over 3 hours (0.05 U/5-minute sample). The delta of the positive temporary basal rate 162 of +50% (i.e., 0.6 U/hr or 0.05 U/5-minute sample) is disregarded. Thus, the maximum insulin delivery rate 166 is calculated as[(300% of default basal rate)+extended bolus rate]=[(300% of 0.1)+0.05]=0.35 U per 5-minute sample. Referring to the above described alternatives, using alternative (i), the maximum delivery amount is calculated as (300% of total programmed delivery)=(300% of 0.2)=0.6 U per 5-minute sample. Using alternative (ii), the maximum delivery rate is calculated as (300% of total basal rate (not including extended bolus))= 300% of 0.15=0.45 U per 5-minute sample. Both results are overly aggressive and can result in hypoglycemia.

Figure 5F:
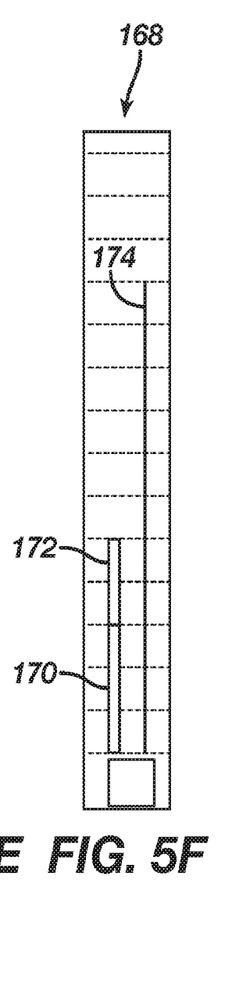

Finally, FIG. 5F illustrates an example 168 in which both a negative temporary basal rate is applied resulting in a total basal rate 170 and the extended bolus 172 is active. In this example, with a basal rate of 1.2 U/hr (0.1 U/5-minute sample) and a negative temporary basal rate of −25%, the resulting total basal rate 160 is 0.9 U/hr, which is equivalent to 0.075 U/5-minute sample. The extended bolus 172 is 1.8 U over 3 hours, which is equivalent to 0.05 U/5-minute sample. Thus, the maximum insulin delivery rate 174 is calculated as [(300% of total basal rate)+extended bolus rate]=[(300% of 0.075)+0.05]=0.275 U per 5-minute sample. Referring to the above alternatives, using alternative (i) the maximum insulin delivery rate is calculated as 300% of total programmed delivery=300% of 0.125=0.375 U per 5-minute sample. Again, this result is overly aggressive and can result in hypoglycemia.

While particular variations and illustrative figures have been used in the foregoing description, those of ordinary skill in the art will recognize that the variations and figures are not intended to be limiting. In addition, where methods and steps described above indicate certain events occurring in certain order, those of ordinary skill in the art will recognize that the ordering of certain steps may be modified and that such modifications are in accordance with those as would be apparent to a person of suitable skill in the field. Additionally, certain of the steps may be performed concurrently in a parallel process when possible, as well as performed sequentially as described above. Therefore, to the extent there are variations, which are within the spirit of the disclosure or equivalent to recited features in the claims, it is the intent that this patent will cover those variations as well.

What is claimed is:

1. A method for determining a maximum insulin delivery rate (MR) for a closed loop insulin management system comprising:
   (a) providing a drug delivery device having a controller that is configured to deliver insulin to a subject at predetermined time intervals based on a default basal rate of insulin delivery (DBR) programmed into the drug delivery device;
   (b) calculating, by the controller, the maximum insulin delivery rate (MR) by:
      (i) determining if a temporary basal insulin delivery is being delivered to a user at a temporary basal insulin delivery rate, the temporary basal insulin delivery rate being a temporary modification of the default basal rate of insulin delivery (DBR) for a shortened period of time based on factors including illness or exercise, in lieu of the default basal rate of insulin delivery (DBR) programmed at a predetermined time interval;
      (ii) determining, if the temporary basal insulin delivery is being delivered, if a total basal rate of insulin delivery (TBR) is less than or greater than the default basal rate of insulin delivery (DBR);
      (iii) calculating, if it is determined that the total basal rate of insulin delivery (TBR) is less than the default basal rate of insulin delivery (DBR), and setting by the controller the maximum insulin delivery rate (MR) to a predetermined percentage of the total basal rate of insulin delivery (TBR);

(iv) calculating, if it is determined that the total basal rate of insulin delivery (TBR) is greater than the default basal rate of insulin delivery (DBR), and setting by the controller the maximum insulin delivery rate (MR) to a predetermined percentage of the default basal rate of insulin delivery (DBR); and (c) delivering, by the drug delivery device, insulin at the calculated maximum insulin delivery rate.

2. The method of claim 1, further comprising:

prior to calculating and setting the maximum insulin delivery rate (MR), determining if an extended insulin bolus amount is being delivered to a user at an extended bolus delivery rate (EBR); and if an extended insulin bolus amount is being delivered at the extended bolus delivery rate (EBR), and the total basal rate of insulin delivery (TBR) is less than the default basal rate of insulin delivery (DBR), then calculating and setting, by the controller, the maximum insulin delivery rate (MR) as a percentage of the total basal rate of insulin delivery (TBR) plus the extended bolus delivery rate (EBR) or (MR)=a predetermined percentage of (TBR) +(EBR).

3. The method of claim 1, wherein the processor is programmed with either a PID control algorithm or a model predictive control algorithm.

4. The method of claim 3, wherein the predetermined percentage of the total basal rate of insulin delivery (TBR) is a constant.

5. The method of claim 1, wherein the maximum insulin delivery rate (MR) is 300% of the total basal rate of insulin delivery (TBR).

6. A system for management of diabetes, comprising:

a continuous glucose monitor configured to provide a user's glucose levels at each interval in the form of glucose management data;

an insulin infusion pump to deliver insulin; and a controller operatively coupled to the pump and glucose monitor in which the controller is configured to predict at least one future glucose value based on prior glucose measurement data from the continuous glucose monitor and to determine a maximum insulin delivery rate for the insulin infusion pump at uniform time intervals based on a default basal insulin delivery rate that corresponds to a basal rate programmed for administration by the controller at predetermined time intervals and a temporary basal insulin delivery rate, which is a temporary modification of the default basal delivery rate over a shortened period of time based on factors, said factors including exercise or illness and, optionally, an extended bolus delivery rate.

7. The system of claim 6, wherein the controller utilizes a model predictive control algorithm (MPC).

8. The method of claim 1, wherein the controller utilizes a model predictive control algorithm (MPC).

9. A method for determining a maximum insulin delivery rate (MR) for a closed loop insulin management system comprising:

(a) providing a drug delivery device having a controller that is configured to deliver insulin to a subject at predetermined time intervals over an extended period based on a default basal rate of insulin delivery (DBR), the default basal rate of insulin delivery corresponding to a basal rate programmed for administration at predetermined time intervals by the controller;

(b) calculating, by the controller, the maximum insulin delivery rate (MR) by:

(i) determining if a temporary basal insulin delivery is being delivered to a user, the temporary basal insulin delivery being a modification of the default basal rate of insulin delivery (DBR) for a shortened period based on factors, said factors including exercise or illness;

(ii) calculating, if it is determined no temporary basal insulin delivery is being delivered, and setting by the controller the maximum insulin delivery rate (MR) to be a predetermined percentage of the default basal rate of insulin delivery (DBR);

and (c) delivering, by the drug delivery device, insulin at the calculated maximum insulin delivery rate (MR).

10. A method for determining a maximum insulin delivery rate (MR) for a closed loop insulin management system comprising:

(a) providing a drug delivery device having a controller that is configured to deliver insulin to a subject according to a default basal rate of insulin delivery (DBR) at predetermined time intervals over an extended period of time, the default basal rate of insulin delivery (DBR) corresponding to a basal rate programmed for administration by the controller at predetermined time intervals;

(b) calculating, by the controller, a maximum insulin delivery rate (MR) by:

(i) determining if a temporary basal insulin delivery is being delivered to a user, the temporary basal insulin delivery being a temporary modification of the default basal rate of insulin delivery (DBR) over a shortened time period, the temporary insulin delivery being based on factors including exercise or illness;

(ii) determining, if the temporary basal insulin delivery is being delivered, if a total basal rate of insulin delivery (TBR) is less than or greater than the default rate of insulin delivery (DBR);

and (iii) calculating, if it is determined the total basal rate of insulin delivery (TBR) is less than the default basal rate of insulin delivery (DBR), and setting, by the controller, of the maximum insulin delivery rate (MR) as a percentage of the total basal rate of insulin delivery (TBR) or MR=a predetermined percentage of the total basal rate of insulin delivery (TBR); and (c) delivering, by the drug delivery device, insulin at the calculated maximum insulin delivery rate (MR).

* * * * *